United States Patent
Van Laar et al.

(10) Patent No.: US 7,741,522 B2
(45) Date of Patent: Jun. 22, 2010

(54) DIRECT AMINATION OF HYDROCARBONS

(75) Inventors: Frederik Van Laar, Dubai (AE);
Ekkehard Schwab, Neustadt (DE);
Joachim-Thierry Anders, Goennheim (DE); Sven Crone, Limburgerhof (DE);
Karl Hoelemann, Mannheim (DE);
Wolfgang Mackenroth, Tervuren (BE);
Petr Kubanek, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 4 days.

(21) Appl. No.: 12/280,634

(22) PCT Filed: Feb. 15, 2007

(86) PCT No.: PCT/EP2007/051473

§ 371 (c)(1),
(2), (4) Date: Aug. 25, 2008

(87) PCT Pub. No.: WO2007/096297

PCT Pub. Date: Aug. 30, 2007

(65) Prior Publication Data

US 2009/0023956 A1      Jan. 22, 2009

(30) Foreign Application Priority Data

Feb. 24, 2006   (EP)   .................................. 06110416

(51) Int. Cl.
*C07C 209/02* (2006.01)
(52) U.S. Cl. ..................................................... 564/408
(58) Field of Classification Search .................. 564/408
See application file for complete search history.

(56) References Cited

U.S. PATENT DOCUMENTS

| 3,919,155 | A | 11/1975 | Squire |
| 3,929,889 | A | 12/1975 | Squire |
| 4,001,260 | A | 1/1977 | Del Pesco |
| 4,031,106 | A | 6/1977 | DelPesco |
| 6,204,411 | B1 | 3/2001 | Axon et al. |
| 6,281,387 | B1 | 8/2001 | Bhasin et al. |
| 2001/0044557 | A1 | 11/2001 | Bhasin et al. |

FOREIGN PATENT DOCUMENTS

| CA | 553998 | 3/1958 |
| CN | 1555921 | 12/2004 |
| DE | 196 34 110 | 2/1998 |
| WO | 99 10311 | 3/1999 |
| WO | 00 09473 | 2/2000 |
| WO | 00 69804 | 11/2000 |
| WO | 01 32600 | 5/2001 |
| WO | 2007 025882 | 3/2007 |

OTHER PUBLICATIONS

Hagemeyer, Alfred et al., "Application of combinatorial catalysis for the direct amination of benzene to aniline", Applied Catalysis A: General, Elsevier, vol. 227, No. 1-2, pp. 43-61, XP004340850, (2002).

Wibaut, J. P., "Zur Bildung von Anilin aus Ammoniak und Benzol bei hohen Temperaturen und bei Anwesenheit von Kontaktsubstanzen", Berichte, pp. 541-546, (1917).

*Primary Examiner*—Brian J Davis
(74) *Attorney, Agent, or Firm*—Oblon, Spivak, McClelland, Maier & Neustadt, L.L.P.

(57) ABSTRACT

A process for aminating hydrocarbons with ammonia in the presence of catalyst (i) which catalyzes the amination, which comprises supplying oxidizing agent to the reaction mixture and reacting the oxidizing agent with hydrogen which is formed in the amination in the presence of a catalyst (ii) which catalyzes this reaction with hydrogen.

20 Claims, No Drawings

DIRECT AMINATION OF HYDROCARBONS

The invention relates to a process for preferably continuously aminating, preferably directly aminating hydrocarbons, preferably by reacting hydrocarbons, more preferably aromatic hydrocarbons, in particular benzene, with ammonia, in the presence of catalyst (i) which catalyzes the amination, wherein oxidizing agents, preferably air, oxygen, CO, $CO_2$, NO and/or $NO_2O$, more preferably oxygen, are supplied to the reaction mixture, and the oxidizing agent is reacted with hydrogen which forms in the amination in the presence of a catalyst (ii) which catalyzes this reaction with hydrogen. In particular, the invention relates to processes for aminating hydrocarbons, preferably by reacting aromatic hydrocarbons, more preferably benzene, with ammonia, especially according to the following reaction, which is preferably catalyzed:

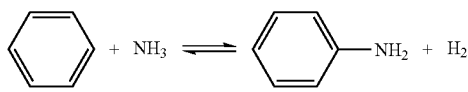

The commercial preparation of amines, especially of aromatic amines such as aniline, is typically carried out in multistage reactions. Aniline is prepared, for example, typically by converting benzene to a benzene derivative, for example nitrobenzene, chlorobenzene or phenol, and subsequently converting this derivative to aniline.

More advantageous than such indirect processes for preparing especially aromatic amines are methods which enable direct preparation of the amines from the corresponding hydrocarbons. A very elegant route is that of heterogeneously catalyzed direct amination of benzene, described for the first time in 1917 by Wibaut (Berichte, 50, 541-546). Since direct amination is equilibrium-limited, several systems have been described which shift the equilibrium limit by the selective removal of hydrogen from the reaction and enable increased benzene conversion. Most processes are based on the use of metal oxides which are reduced by hydrogen, hence removing the hydrogen from the reaction system and thus shifting the equilibrium.

CN 1555921A discloses the oxidoamination of benzene in the liquid phase, hydrogen peroxide functioning as the "O" donor. However, the use of $H_2O_2$ is suitable only to a limited extent for commodity chemicals owing to the cost and the low selectivity owing to subsequent reactions.

CA 553,988 discloses a process for preparing aniline from benzene, in which benzene, ammonia and gaseous oxygen are reacted over a platinum catalyst at a temperature of about 1000° C. Suitable platinum-comprising catalysts are platinum alone, platinum with certain specific metals and platinum together with certain specific metal oxides. In addition, CA 553,988 discloses a process for preparing aniline, in which benzene in the gas phase is reacted with ammonia in the presence of a reducible metal oxide at temperatures of from 100 to 1000° C., without addition of gaseous oxygen. Suitable reducible metal oxides are the oxides of iron, nickel, cobalt, tin, antimony, bismuth and copper.

U.S. Pat. No. 3,919,155 relates to the direct amination of aromatic hydrocarbons with ammonia, the catalyst used being nickel/nickel oxide which may additionally comprise oxides and carbonates of zirconium, strontium, barium, calcium, magnesium, zinc, iron, titanium, aluminum, silicon, cerium, thorium, uranium and alkali metals.

U.S. Pat. No. 3,929,889 likewise relates to the direct amination of aromatic hydrocarbons with ammonia over a nickel/nickel oxide catalyst, the catalyst used having been reduced partly to elemental nickel and subsequently reoxidized to obtain a catalyst which has a ratio of nickel:nickel oxide of from 0.001:1 to 10:1.

U.S. Pat. No. 4,001,260 discloses a process for directly aminating aromatic hydrocarbons with ammonia, a nickel/nickel oxide catalyst again being used, which has been applied to zirconium dioxide and has been reduced with ammonia before use in the amination reaction.

U.S. Pat. No. 4,031,106 relates in turn to the direct amination of aromatic hydrocarbons with ammonia over a nickel/nickel oxide catalyst on a zirconium dioxide support which also comprises an oxide selected from lanthanoids and rare earth metals.

DE 196 34 110 describes nonoxidative amination at a pressure of 10-500 bar and a temperature of 50-900° C., the reaction being effected in the presence of an acidic heterogeneous catalyst which has been modified with light and heavy platinum group metals.

WO 00/09473 describes a process for preparing amines by directly aminating aromatic hydrocarbons over a catalyst comprising at least one vanadium oxide.

WO 99/10311 teaches a process for directly aminating aromatic hydrocarbons at a temperature of <500° C. and a pressure of <10 bar. The catalyst used is a catalyst comprising at least one metal selected from transition metals, lanthanides and actinides, preferably Cu, Pt, V, Rh and Pd. To increase the selectivity and/or the conversion, preference is given to performing the direct amination in the presence of an oxidizing agent.

WO 00/69804 relates to a process for directly aminating aromatic hydrocarbons using, as a catalyst, a complex comprising a noble metal and a reducible metal oxide.

Particular preference is given to catalysts comprising palladium and nickel oxide or palladium and cobalt oxide.

Most of the processes mentioned start from a mechanism for direct amination as detailed in the abstract of WO 00/69804. This is followed first by the (noble) metal-catalyzed preparation of the desired amine compound from the aromatic hydrocarbon and ammonia, and, in a second step, by the "scavenging" of the hydrogen formed in the first step with a reducible metal oxide. The same mechanistic considerations form the basis of the process in WO 00/09473, in which the hydrogen is scavenged with oxygen from vanadium oxides (page 1, lines 30 to 33). The same mechanism is also the basis of U.S. Pat. No. 4,001,260, as is evident from the remarks and the diagram in column 2, lines 16 to 44.

It is an object of the present invention to develop a particularly economically viable process for aminating hydrocarbons, in particular a process for reacting benzene with ammonia, in which a preferably continuous process is enabled with very high selectivity and/or very high conversion.

This object is achieved by supplying oxidizing agent, preferably air, oxygen, CO, $CO_2$, NO and/or $N_2O$, more preferably oxygen, to the reaction mixture and reacting the oxidizing agent with hydrogen which is formed in the amination in the presence of a catalyst (ii) which catalyzes this reaction with hydrogen.

It has been found that, surprisingly, the conversion in the direct amination over metal catalysts (for example Ni, Fe, Co, Cu, NM or alloys thereof, where NM represents noble metals), compared with the equilibrium conversion, was considerably increased when the hydrogen formed in the reaction of the hydrocarbon with the ammonia is removed by using oxidizing agents and their reaction with the hydrogen in the presence of appropriate catalysts. Surprisingly, it was found that the use of the catalyst (ii) does not adversely affect the direct amination but increases the conversion by the more rapid removal of the hydrogen.

In the known metal-metal oxide systems described at the outset, the cataloreactant has to be loaded again with "oxygen" after a certain time. This means costly interruptions, since the amination and the reactivation typically do not proceed under the same conditions (pressure and temperature). The reactor thus has to be decompressed, purged and inertized, and the catalyst has to be reactivated and brought back under reaction conditions. The selectivity of the entire reaction changes with the oxygen content of the cataloreactant and thus has to be compensated by process alteration (pressure, ammonia-aromatic ratio and/or temperature). A sufficient selectivity for the carbon and also nitrogen balance cannot be achieved with these systems, since ammonia is combusted at the surface to form $N_2$ and $H_2O$ by the metal oxides or by adsorbed oxygen. The provision of a fully integrated solution can thus be accomplished with difficulty, if at all, with metal oxide systems.

These disadvantages are avoided by the inventive removal of the hydrogen from the reaction system. The process according to the invention thus enables very efficient, selective, inexpensive direct amination.

According to the invention, oxidizing agents, preferably air, oxygen, CO, $CO_2$, NO and/or $N_2O$, more preferably oxygen, are supplied to the reaction mixture and reacted with hydrogen which is formed in the amination in the presence of the catalyst (ii). The oxidizing agent can be introduced into the reaction zone of the reactor in the process according to the invention together with further coreactants, cocatalysts or further reagents if appropriate, in each case depending on the amination performed. For example, in the amination of benzene, oxygen or an oxygen-comprising gas can be introduced into the reaction zone of the reactor as a coreactant. The relative amount of the gaseous oxygen which can be introduced into the reaction zone is variable and depends, inter alia, upon the catalyst system used. The molar ratio of gaseous oxygen to benzene may, for example, be in the range from 0.05:1 to 1:1, preferably from 0.1:1 to 0.5:1.

According to the invention, the hydrogen formed in the amination is reacted with the oxidizing agent. It may therefore be viable, in the process, first to react the hydrocarbon with ammonia in the presence of the catalyst (i) and then to supply the oxidizing agent to the reaction mixture. Homogeneous mixing of the two catalysts (i) and (ii) can be employed, but preference is given first to initially charging an amination zone with the catalyst (i) and then to increasing the content of catalyst (ii) in the reaction mixture. In this case, the oxidizing agent can be added together with the feed, i.e. the benzene and the ammonia. However, preference is given to not adding the oxidizing agent until downstream of a first amination zone or at one or more points.

The procedure can thus preferably be to first react the hydrocarbon with ammonia in the presence of the catalyst (i) and then, in the presence of the catalyst (ii), to remove the hydrogen formed from the reaction mixture with the oxidizing agent, hydrocarbon reacting with ammonia in the presence of the catalyst (i) during or after the hydrogen oxidation. Particular preference is given to effecting the process according to the invention such that, in a first reaction chamber, for example a reactor or part of a reactor, hydrocarbon is reacted with ammonia in the presence of the catalyst (i), then the oxidizing agent is supplied to the reaction mixture and, in a subsequent reaction chamber, for example a reactor or part of a reactor, the oxidizing agent is reacted with the hydrogen formed in the amination in the presence of the compound (ii) which catalyzes this reaction with hydrogen, hydrocarbon reacting with ammonia in the presence of the catalyst (i) during or after the hydrogen oxidation. The process may be configured such that the catalysts (i) and (ii) are each present in separate catalyst beds, the oxidizing agent is supplied to the reaction mixture upstream of a catalyst bed comprising the catalyst (ii), and the catalyst bed comprising the catalyst (ii) is followed by a catalyst bed comprising the catalyst (i). This can in turn be followed by a catalyst bed comprising the catalyst (ii).

The process according to the invention, i.e. the amination of hydrocarbons, especially the reaction of benzene with ammonia, is carried out in the presence of compounds which catalyze the amination (catalysts (i)).

The catalysts (i) used may be the catalysts known for the direct amination of hydrocarbons, especially those known for the direct amination of benzene with ammonia to give aniline. Such catalysts have been described in a wide variety in the patent literature and are commonly known. Since, in the process according to the invention, the hydrogen is removed by reaction with oxidizing agents supplied specially, it is also possible to use catalysts which have components which are not reactive toward hydrogen. Useful catalysts include, for example, customary metal catalysts, for example those based on nickel, iron, cobalt, copper, noble metals or alloys of these metals mentioned. Useful noble metals (NM) may include all noble metals, for example Ru, Rh, Pd, Ag, Ir, Pt and Au, the noble metals Ru and Rh preferably not being used alone but rather in alloy with other transition metals, for example Co, Cu, Fe and nickel or mixtures thereof. Such alloys are also used with preference in the case of use of the other noble metals; for example, supported NiCuNM; CoCuNM; NiCoCuNM, NiMoNM, NiCrNM, NiReNM, CoMoNM, CoCrNM, CoReNM, FeCuNM, FeCoCuNM, FeMoNM, FeReNM alloys are of interest, where NM is a noble metal, especially preferably Ag and/or Au.

The catalyst may be used in generally customary form, for example as a powder or as a system usable in a fixed bed (for example extrudates, spheres, tablets, rings), in which case the catalytically active constituents may, if appropriate, be present on a support material. Useful support materials include, for example, inorganic oxides, for example $ZrO_2$, $SiO_2$, $Al_2O_3$, MgO, $TiO_2$, $B_2O_3$, CaO, ZnO, BaO, $ThO_2$, $CeO_2$, $Y_2O_3$ and mixtures of these oxides, e.g. magnesium aluminum oxide, preferably $TiO_2$, $ZrO_2$, $Al_2O_3$, magnesium aluminum oxide and $SiO_2$, more preferably $ZrO_2$ and magnesium aluminum oxide. $ZrO_2$ is understood to mean either pure $ZrO_2$ or the normal Hf-comprising $ZrO_2$.

The catalysts used with preference in the process according to the invention may be regenerated, for example by passing a reductive atmosphere (for example $H_2$ atmosphere) over the catalyst or first an oxidative and then a reductive atmosphere over or through the catalyst bed.

The catalyst (i) used will preferably comprise compounds which comprise Ni, Co, Fe, Cu or combinations of these elements; the catalyst (i) used preferably comprises compounds which comprise Ni—Cu—X, Fe—Cu—X and/or Co—Cu—X, where X is Ag or Mo, more preferably the combination of Ni—Cu and/or Fe—Cu, in particular their combination with an additional doping element Ni—Cu—X, Fe—Cu—X, where X is Ag or Mo. Especially preferred are alloys of NiCu (Ag or Mo) and/or FeCu (Ag or Mo). The catalysts, i.e. the elements in catalyst (i), may be present in reduced or else in oxidized form.

In the catalyst (i), the proportion by weight of the elements Ni, Co and Fe together, i.e. the proportion of the total weight of these elements, not all elements necessarily being present in the catalyst, is preferably between 0.1% by weight and 75% by weight, more preferably between 1% by weight and 70% by weight, in particular between 2% by weight and 50% by weight, and the proportion by weight of Cu is between 0.1% by weight and 75% by weight, preferably between 0.1% by weight and 25% by weight, more preferably between 0.1% by weight and 20% by weight, in particular between 2.5% by weight and 10% by weight, based on the total weight of catalyst (i). In addition, catalyst (i) may comprise support material.

The proportion by weight of the doping element X in the total weight of catalyst (i) is preferably between 0.01% by weight and 8% by weight, more preferably between 0.1% by weight and 5% by weight, in particular between 0.5% by weight and 4% by weight.

The catalyst bed comprising catalysts (i) and (ii) is preferably loaded at from 0.1 to 5 kg, preferably from 0.2 to 2 kg, in particular from 0.3 to 1.5 kg of hydrocarbon per liter of catalyst bed and per hour. Catalysts (i) and (ii) are preferably different; catalysts (i) and (ii) are preferably different in material terms; in particular, catalyst (i) comprises elements that catalyst (ii) does not comprise.

According to the invention, one or more catalysts (ii) are used in order to remove the hydrogen formed in the amination from the reaction system. It is possible to use generally customary and known catalysts which catalyze the oxidation of hydrogen, preferably those which catalyze the reaction of oxygen with hydrogen. Such catalysts are common knowledge and have been described many times. The catalyst (ii) used preferably comprises compounds comprising Pt and/or Pd/Ag, more preferably those which comprise Pt and/or Pd/Ag, i.e. Pd and Ag, on a support, especially pure $SiO_2$, pure $Al_2O_3$, $ZrO_2$ and/or pure $TiO_2$ as the support. As "pure" are understood those supports which comprise impurities <0.5% by weight. More preferably, in the catalyst (ii), the proportion by weight of Pt is between 0.0001% by weight and 1% by weight, preferably between 0.001% by weight and 0.5% by weight, in particular between 0.01% by weight and 0.1% by weight, based on the total weight of the catalyst.

It is possible with the amination process according to the invention to aminate any hydrocarbons, such as aromatic hydrocarbons, aliphatic hydrocarbons and cycloaliphatic hydrocarbons, which may have any substitution and may have heteroatoms and double or triple bonds within their chain or their ring/their rings. In the amination process according to the invention, preference is given to using aromatic hydrocarbons and heteroaromatic hydrocarbons. The particular products are the corresponding arylamines or heteroarylamines.

In the context of the present invention, an aromatic hydrocarbon is understood to mean an unsaturated cyclic hydrocarbon which has one or more rings and comprises exclusively aromatic C—H bonds. The aromatic hydrocarbon preferably has one or more 5- or 6-membered rings.

A heteroaromatic hydrocarbon is understood to mean those aromatic hydrocarbons in which one or more of the carbon atoms of the aromatic ring is/are replaced by a heteroatom selected from N, O and S.

The aromatic hydrocarbons or the heteroaromatic hydrocarbons may be substituted or unsubstituted. A substituted aromatic or heteroaromatic hydrocarbon is understood to mean compounds in which one or more hydrogen atoms which is/are bonded to a carbon atom or heteroatom of the aromatic ring is/are replaced by another radical. Such radicals are, for example, substituted or unsubstituted alkyl, alkenyl, alkynyl, heteroalkyl, heteroalkenyl, heteroalkynyl, cycloalkyl and/or cycloalkynyl radicals. In addition, the following radicals are possible: halogen, hydroxyl, alkoxy, aryloxy, amino, amido, thio and phosphino. Preferred radicals of the aromatic or heteroaromatic hydrocarbons are selected from $C_{1-6}$-alkyl, $C_{1-6}$-alkenyl, $C_{1-6}$-alkynyl, $C_{3-8}$-cycloalkyl, $C_{3-8}$-cycloalkenyl, alkoxy, aryloxy, amino and amido, where $C_{1-6}$ relates to the number of carbon atoms in the main chain of the alkyl radical, of the alkenyl radical or of the alkynyl radical, and $C_{3-8}$ to the number of carbon atoms of the cycloalkyl or cycloalkenyl ring. It is also possible that the substituents (radicals) of the substituted aromatic or heteroaromatic hydrocarbon have further substituents.

The number of substituents (radicals) of the aromatic or heteroaromatic hydrocarbon is arbitrary. In a preferred embodiment, the aromatic or heteroaromatic hydrocarbon has, however, at least one hydrogen atom which is bonded directly to a carbon atom or a heteroatom of the aromatic ring. Thus, a 6-membered ring preferably has 5 or fewer substituents (radicals) and a 5-membered ring preferably has 4 or fewer substituents (radicals). A 6-membered aromatic or heteroaromatic ring more preferably bears 4 or fewer substituents, even more preferably 3 or fewer substituents (radicals). A 5-membered aromatic or heteroaromatic ring preferably bears 3 or fewer radicals, more preferably 2 or fewer radicals.

In a particularly preferred embodiment of the process according to the invention, an aromatic or heteroaromatic hydrocarbon of the general formula $(A)-(B)_n$ is used, where the symbols are each defined as follows:

A is independently aryl or heteroaryl, A is preferably selected from phenyl, diphenyl, diphenylmethane, benzyl, dibenzyl, naphthyl, anthracene, pyridyl and quinoline;

n is from 0 to 5, preferably from 0 to 4, especially in the case when A is a 6-membered aryl or heteroaryl ring; in the case that A is a 5-membered aryl or heteroaryl ring, n is preferably from 0 to 4; irrespective of the ring size, n is more preferably from 0 to 3, most preferably from 0 to 2 and in particular from 0 to 1; the remaining hydrocarbon atoms or heteroatoms of A which do not bear any substituents B bear hydrogen atoms, or, if appropriate, no substituents;

B is independently selected from the group consisting of alkyl, alkenyl, alkynyl, substituted alkyl, substituted alkenyl, substituted alkynyl, heteroalkyl, substituted heteroalkyl, heteroalkenyl, substituted heteroalkenyl, heteroalkynyl, substituted heteroalkynyl, cycloalkyl, cycloalkenyl, substituted cycloalkyl, substituted cycloalkenyl, halogen, hydroxy, alkoxy, aryloxy, carbonyl, amino, amido, thio and phosphino; B is preferably independently selected from $C_{1-6}$-alkyl, $C_{1-6}$-alkenyl, $C_{1-6}$-alkynyl, $C_{3-8}$-cycloalkyl, $C_{3-8}$-cycloalkenyl, alkoxy, aryloxy, amino and amido.

The term "independently" means that, when n is 2 or greater, the substituents B may be identical or different radicals from the groups mentioned.

In the present application, alkyl is understood to mean branched or unbranched, saturated acyclic hydrocarbyl radicals. Examples of suitable alkyl radicals are methyl, ethyl, n-propyl, i-propyl, n-butyl, t-butyl, i-butyl, etc. The alkyl radicals used preferably have from 1 to 50 carbon atoms, more preferably from 1 to 20 carbon atoms, even more preferably from 1 to 6 carbon atoms and in particular from 1 to 3 carbon atoms.

In the present application, alkenyl is understood to mean branched or unbranched, acyclic hydrocarbyl radicals which have at least one carbon-carbon double bond. Suitable alkenyl radicals are, for example, 2-propenyl, vinyl, etc. The alkenyl radicals have preferably from 2 to 50 carbon atoms, more preferably from 2 to 20 carbon atoms, even more preferably from 2 to 6 carbon atoms and in particular from 2 to 3 carbon atoms. The term alkenyl also encompasses radicals which have either a cis-orientation or a trans-orientation (alternatively E or Z orientation).

In the present application, alkynyl is understood to mean branched or unbranched, acyclic hydrocarbyl radicals which have at least one carbon-carbon triple bond. The alkynyl radicals preferably have from 2 to 50 carbon atoms, more preferably from 2 to 20 carbon atoms, even more preferably from 1 to 6 carbon atoms and in particular from 2 to 3 carbon atoms.

Substituted alkyl, substituted alkenyl and substituted alkynyl are understood to mean alkyl, alkenyl and alkynyl radicals in which one or more hydrogen atoms which are bonded to one carbon atom of these radicals are replaced by another group. Examples of such other groups are heteroatoms, halogen, aryl, substituted aryl, cycloalkyl, cycloalkenyl, substituted cycloalkyl, substituted cycloalkenyl and combinations thereof. Examples of suitable substituted alkyl radicals are benzyl, trifluoromethyl, inter alia.

The terms heteroalkyl, heteroalkenyl and heteroalkynyl are understood to mean alkyl, alkenyl and alkynyl radicals in which one or more of the carbon atoms in the carbon chain is replaced by a heteroatom selected from N, O and S. The bond between the heteroatom and a further carbon atom may be saturated, or, if appropriate, unsaturated.

In the present application, cycloalkyl is understood to mean saturated cyclic nonaromatic hydrocarbyl radicals which are composed of a single ring or a plurality of fused rings. Suitable cycloalkyl radicals are, for example, cyclopentyl, cyclohexyl, cyclooctanyl, bicyclooctyl, etc. The cycloalkyl radicals have preferably between 3 and 50 carbon atoms, more preferably between 3 and 20 carbon atoms, even more preferably between 3 and 8 carbon atoms and in particular between 3 and 6 carbon atoms.

In the present application, cycloalkenyl is understood to mean partly unsaturated, cyclic nonaromatic hydrocarbyl radicals which have a single fused ring or a plurality of fused rings. Suitable cycloalkenyl radicals are, for example, cyclopentenyl, cyclohexenyl, cyclooctenyl, etc. The cycloalkenyl radicals have preferably from 3 to 50 carbon atoms, more preferably from 3 to 20 carbon atoms, even more preferably from 3 to 8 carbon atoms and in particular from 3 to 6 carbon atoms.

Substituted cycloalkyl and substituted cycloalkenyl radicals are cycloalkyl and cycloalkenyl radicals, in which one or more hydrogen atoms of any carbon atom of the carbon ring is replaced by another group. Such other groups are, for example, halogen, alkyl, alkenyl, alkynyl, substituted alkyl, substituted alkenyl, substituted alkynyl, aryl, substituted aryl, cycloalkyl, cycloalkenyl, substituted cycloalkyl, substituted cycloalkenyl, an aliphatic heterocyclic radical, a substituted aliphatic heterocyclic radical, heteroaryl, substituted heteroaryl, alkoxy, aryloxy, boryl, phosphino, amino, silyl, thio, seleno and combinations thereof. Examples of substituted cycloalkyl and cycloalkenyl radicals are 4-dimethylaminocyclohexyl, 4,5-dibromocyclohept-4-enyl, inter alia.

In the context of the present application, aryl is understood to mean aromatic radicals which have a single aromatic ring or a plurality of aromatic rings which are fused, joined via a covalent bond or joined by a suitable unit, for example a methylene or ethylene unit. Such suitable units may also be carbonyl units, as in benzophenol, or oxygen units, as in diphenyl ether, or nitrogen units, as in diphenylamine. The aromatic ring or the aromatic rings are, for example, phenyl, naphthyl, diphenyl, diphenyl ether, diphenylamine and benzophenone. The aryl radicals preferably have from 6 to 50 carbon atoms, more preferably from 6 to 20 carbon atoms, most preferably from 6 to 8 carbon atoms.

Substituted aryl radicals are aryl radicals in which one or more hydrogen atoms which are bonded to carbon atoms of the aryl radical are replaced by one or more other groups. Suitable other groups are alkyl, alkenyl, alkynyl, substituted alkyl, substituted alkenyl, substituted alkynyl, cycloalkyl, cycloalkenyl, substituted cycloalkyl, substituted cycloalkenyl, heterocyclo, substituted heterocyclo, halogen, halogen-substituted alkyl (e.g. $CF_3$), hydroxyl, amino, phosphino, alkoxy, thio and both saturated and unsaturated cyclic hydrocarbons which may be fused on the aromatic ring or on the aromatic rings or may be joined by a bond, or may be joined to one another via a suitable group. Suitable groups have already been mentioned above.

According to the present application, heterocyclo is understood to mean a saturated, partly unsaturated or unsaturated, cyclic radical in which one or more carbon atoms of the radical are replaced by a heteroatom, for example N, O or S. Examples of heterocyclo radicals are piperazinyl, morpholinyl, tetrahydropyranyl, tetrahydrofuranyl, piperidinyl, pyrrolidinyl, oxazolinyl, pyridyl, pyrazyl, pyridazyl, pyrimidyl.

Substituted heterocyclo radicals are those heterocyclo radicals in which one or more hydrogen atoms which are bonded to one of the ring atoms are replaced by another group. Suitable other groups are halogen, alkyl, substituted alkyl, aryl, substituted aryl, heteroaryl, substituted heteroaryl, alkoxy, aryloxy, boryl, phosphino, amino, silyl, thio, seleno and combinations thereof.

Alkoxy radicals are understood to mean radicals of the general formula —$OZ^1$ in which $Z^1$ is selected from alkyl, substituted alkyl, cycloalkyl, substituted cycloalkyl, heterocycloalkyl, substituted heterocycloalkyl, silyl and combinations thereof. Suitable alkoxy radicals are, for example, methoxy, ethoxy, benzyloxy, t-butoxy, etc. The term aryloxy is understood to mean those radicals of the general formula —$OZ^1$ in which $Z^1$ is selected from aryl, substituted aryl, heteroaryl, substituted heteroaryl and combinations thereof. Suitable aryloxy radicals are phenoxy, substituted phenoxy, 2-pyridinoxy, 8-quinolinoxy, inter alia.

Amino radicals are understood to mean radicals of the general formula —$NZ^1Z^2$ in which $Z^1$ and $Z^2$ are each independently selected from hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

Aromatic or heteroaromatic hydrocarbons used with preference in the amination process according to the invention are selected from benzene, diphenylmethane, naphthalene, anthracene, toluene, xylene, phenol and aniline, and also pyridine, pyrazine, pyridazine, pyrimidine and quinoline. It is also possible to use mixtures of the aromatic or heteroaromatic hydrocarbons mentioned. Particular preference is given to using the aromatic hydrocarbons, benzene, naphthalene, anthracene, toluene, xylene, pyridine, phenol and aniline, very particular preference to using benzene, toluene and pyridine.

Especially preferably, benzene is used in the amination process according to the invention, so that the product formed is aniline.

The compound through which the amino group is introduced is more preferably ammonia. This means that, in accordance with the invention, the hydrocarbons, especially the benzene, are more preferably reacted with ammonia. If appropriate, compounds which eliminate ammonia under the reaction conditions may also find use.

For the preparation of mono- and dialkyl-N,(N)-substituted aromatic amines, for example mono- and/or dimethylaniline, it is also possible to use mono- and dialkylamines, preferably mono- and di(m)ethylamine.

The reaction conditions in the amination processes according to the invention are dependent upon factors including the aromatic hydrocarbon to be aminated and the catalyst used.

The amination, preferably the amination of benzene, i.e. the reaction of benzene with ammonia, is effected generally at temperatures of from 200 to 800° C., preferably from 300 to 700° C., more preferably from 325 to 600° C. and most preferably from 350 to 500° C.

The reaction pressure in the amination, preferably in the amination of benzene, i.e. the reaction of benzene with ammonia, is preferably from 1 to 900 bar, more preferably from 1 to 300 bar, in particular from 5 to 125 bar, especially preferably from 15 to 110 bar.

The residence time in the amination process according to the invention, preferably in the amination of benzene, is generally from 15 minutes to 8 hours, preferably from 15 minutes to 4 hours, more preferably from 15 minutes to 1 hour, in the case of performance in a batchwise process. In the case of performance in a preferred continuous process, the residence time is generally from 0.1 second to 20 minutes, preferably from 0.5 second to 10 minutes. For the preferred continuous processes, "residence time" in this context means the residence time over the catalyst, hence the residence time in the catalyst bed for fixed bed catalyst; for fluidized bed reactors, the synthesis part of the reactor (part of the reactor where the catalyst is localized) is considered.

The relative amount of the hydrocarbon used and of the amine component is dependent upon the amination reaction carried out and the reaction conditions. In general, at least stoichiometric amounts of the hydrocarbon and the amine component are used. However, it is typically preferred to use one of the reaction partners in a stoichiometric excess in order to achieve a shift in the equilibrium to the side of the desired product and hence a higher conversion. Preference is given to using the amine component in a stoichiometric excess.

The amination process according to the invention may be carried out continuously, batchwise or semicontinuously. Suitable reactors are thus both stirred tank reactors and tubular reactors. Typically reactors are, for example, high pressure stirred tank reactors, autoclaves, fixed bed reactors, fluidized bed reactors, moving beds, circulating fluidized beds, salt bath reactors, plate heat exchangers as reactors, tray reactors having a plurality of trays with or without heat exchange or drawing/feeding of substreams between the trays, in possible designs as radial flow or axial flow reactors, continuous stirred tanks, bubble reactors, etc., and the reactor suitable in each case for the desired reaction conditions (such as temperature, pressure and residence time) is used. The reactors may each be used as a single reactor, as a series of individual reactors and/or in the form of two or more parallel reactors. The reactors may be operated in an AB mode (alternating mode). The process according to the invention may be carried out as a batch reaction, semicontinuous reaction or continuous reaction. The specific reactor construction and performance of the reaction may vary depending on the amination process to be carried out, the state of matter of the aromatic hydrocarbon to be aminated, the required reaction times and the nature of the nitrogen-containing catalyst used. Preference is given to carrying out the process according to the invention for direct amination in a high pressure stirred tank reactor, fixed bed reactor or fluidized bed reactor.

In a particularly preferred embodiment, in the amination of benzene to aniline, fixed bed or fluidized bed reactors are used, in which case the membranes are arranged internally and hydrogen is thus removed in the synthesis part. A further advantage of the membrane, which can be flowed through by means of a purge stream, is good thermal control of the reactor: heat of reaction can be added or preferably removed by heating or cooling the purge stream.

The hydrocarbon and the amine component may be introduced in gaseous or liquid form into the reaction zone of the particular reactor. The preferred phase is dependent in each case upon the amination carried out and the reactor used. In a preferred embodiment, for example in the preparation of aniline from benzene, benzene and ammonia are preferably present as gaseous reactants in the reaction zone. Typically, benzene is fed as a liquid which is heated and evaporated to form a gas, while ammonia is present either in gaseous form or in a supercritical phase in the reaction zone. It is likewise possible that benzene is present in a supercritical phase at least together with ammonia.

The hydrocarbon and the amine component may be introduced together into the reaction zone of the reactor, for example as a premixed reactant stream, or separately. In the case of a separate addition, the hydrocarbon and the amine component may be introduced simultaneously, offset in time or successively into the reaction zone of the reactor. Preference is given to adding the amine component and adding the hydrocarbon offset in time.

In addition to the chemical modification of the hydrogen, it can preferably also be removed from the reaction mixture physically.

The expression "physically remove" is understood to mean that the hydrogen escapes physically and preferably selectively from the reaction mixture.

Preference is given to physically removing the hydrogen from the reaction mixture by removing hydrogen from the reaction mixture by means of a hydrogen-permeable, preferably hydrogen-selective, membrane, preferably by virtue of the hydrogen diffusing out of the reaction mixture through the membrane. The diffusion of the hydrogen is preferably driven by the concentration gradient between the reaction system (retentate side) in which hydrogen is preferably formed by the reaction of benzene with ammonia, and the space on the other side of the membrane (permeate side). The hydrogen diffused to the permeate side can be depleted there, i.e. removed, preferably by being transported away, for example by means of gas flow or reduced pressure, and/or by chemical reaction, for example by reduction of an organic compound in the gas phase, for example benzene to cyclohexane, or with formation of water, preferably with an oxygenous gas, for example air, preferably by catalyzed reaction with oxygen and/or air. This maintains or increases the concentration gradient between retentate side and permeate side, which drives the diffusion.

The hydrogen-permeable membrane may preferably be part of a reactor and, for example, may at least partly delimit the reaction chamber in which benzene is preferentially reacted with ammonia. The process according to the invention can preferably thus be effected such that the amination, preferably the reaction of benzene with ammonia, is effected in a membrane reactor with integrated hydrogen removal by means of a hydrogen-permeable membrane.

The membrane preferably has a permeance for hydrogen of greater than 10 $m^3/(m^2 \times h \times bar^n)$, more preferably >50 $m^3/(m^2 \times h \times bar^n)$, where n is theoretically 0.5 and actually between 0.5 and 0.6, and n is thus preferably between 0.5 and 0.6, more preferably n=0.5. The permeance (P) can be calculated from the hydrogen flow rate (in $m^3/(m^2,h)$)) and the partial hydrogen pressures:

$$P = \frac{\text{hydrogen flow rate}}{P^n_{Retentate} - P^n_{Permeate}}$$

The membrane preferably has maximum selectivity for hydrogen. In other words, the membrane is preferably impervious and more preferably has an $H_2/N_2$ selectivity of >1000. The use of such membranes ensures that only a minimum fraction of reactant (hydrocarbon, ammonia) and/or product (especially aniline) passes to the permeate side of the membrane. For the preferred Pd and Pd-alloyed membranes, the reactants and hydrocarbons cannot diffuse through the membrane.

The membrane preferably has a thickness between 0.1 μm and 25 μm, more preferably between 0.5 μm and 10 μm, most preferably between 1 μm and 5 μm.

The membrane may have a self-supporting design. Owing to the generally very high material costs, it may be advantageous to fix the actual membrane on a porous ceramic and/or metallic supporting layer ("composite" membrane). This additionally offers the advantage that the membrane is stabilized and low layer thicknesses are also enabled. Typical membranes can be purchased, for example, from NGK in Japan or from Johnson Matthey.

Examples of suitable membranes include mesoporous inorganic membranes, microporous inorganic membranes, polymer membranes, membranes based on metals of transition group 4 or 5, coated with palladium, nanocrystalline metal membranes, mixed-conducting membranes and preferably membranes based on palladium or palladium alloys.

Mesoporous inorganic membranes are, for example, those having a pore size of less than 50 nm, for example those based on $Al_2O_3$.

Microporous inorganic membranes are, for example, those having a pore size of less than 2 nm, for example those based on ceramic or carbon molecular sieves. Useful ceramic molecular sieve membranes include zeolithic membranes, for example those of the MFI type (ZSM-5 or silicalite) which may if appropriate be supported on $Al_2O_3$, and amorphous membranes, for example those of $SiO_2$. Carbon molecular sieve membranes can be produced by carbonizing organic polymers, for example polyimide.

Polymer membranes are "composite" membranes composed of an impervious hydrogen-selective polymer layer on an inorganic support.

Examples of useful membranes based on metals of transition group 4 and/or 5, which are coated with palladium, are those in which one or preferably two layers of palladium or palladium alloys are present on a nonporous support based on base metal, preferably vanadium, niobium and/or tantalum.

Also useful are membranes of TiN, nanocrystalline metal layers, for example $Al_2O_3$-supported platinum or ruthenium, or amorphous membranes.

Also suitable are mixed-conducting membranes which have both electronic and ionic conductivity.

However, preference is given to membranes which are based on palladium or palladium alloys. Useful alloys are especially alloys of palladium with silver and/or copper. Particular preference is given to membranes based on an alloy comprising palladium and between 23% by weight and 25% by weight of silver based on the total weight of the alloy. The alloy comprises more preferably between 75% by weight and 77% by weight of palladium based on the total weight of the alloy. Particular preference is also given to membranes based on an alloy comprising palladium and between 34% by weight and 46% by weight of copper based on the total weight of the alloy. The alloy comprises more preferably between 54% by weight and 66% by weight of palladium based on the total weight of the alloy. The palladium or the palladium alloy membranes may be doped further with rare earth metals, for example gadolinium. The palladium or the palladium alloy membranes may comprise typical further metals in customary amounts, which do not impair, or at least not significantly, the permeability and selectivity for hydrogen. These preferred membranes too may be present on porous substructures which fix and stabilize the actual membrane. The porous substructure may be based, for example, on ceramic, metal or an organic polymer, for example $TiO_2$ and/or $Al_2O_3$. The production of the preferably impervious metal membrane (preferably palladium or palladium alloy) on a porous support is common knowledge and can be effected, for example, by electroplating, sputtering, CVD (chemical vapor deposition) or preferably commonly known electroless wet-chemical coating.

As already explained, the membrane preferably separates the retentate side (reaction side) from the permeate side, the hydrogen formed on the retentate side passing through the membrane to the permeate side, where the hydrogen is removed by reaction, preferably reaction with oxygen or an oxygenous stream, for example air, preferably in the presence of catalysts, and/or mass transfer, preferably by means of a gas stream ("sweep gas" or purge gas). The selective removal of the hydrogen on the permeate side enables a distinct further reduction in the partial hydrogen pressure on the retentate side of the membrane (=reaction side) and thus enables the desired high benzene conversions (>5 mol %, >10 mol %, >20 mol % based on the amount of benzene added) with high aniline selectivity (>95%, >98%, >99%, aniline selectivity: mol of aniline/sum of all products formed in mol (benzene conversion)).

After the amination, the desired product can be isolated by processes known to those skilled in the art.

EXAMPLE 1

Preparation of Amination Catalyst (i)

The catalyst is prepared in accordance with DE-A 44 28 004:

An aqueous solution of nickel nitrate, copper nitrate and zirconium acetate which comprises 4.48% by weight of Ni (calculated as NiO), 1.52% by weight of Cu (calculated as CuO) and 2.28% by weight of Zr (calculated as $ZrO_2$) is precipitated simultaneously in a stirrer vessel in a constant stream with a 20% aqueous sodium carbonate solution at a temperature of 70° C., in such a way that the pH of 7.0 measured with a glass electrode is maintained. The resulting suspension is filtered and the filtercake is washed with mineralized water until the electrical conductivity of the filtrate is approx. 20 μs. Sufficient ammonium heptamolybdate is then incorporated into the still-moist filtercake that the oxide mixture specified below is obtained. Thereafter, the filtercake is dried at a temperature of 150° C. in a drying cabinet or a spray dryer. The hydroxide-carbonate mixture obtained in this way is then heat-treated at a temperature of from 430 to 460° C. over a period of 4 hours. The oxidic species thus prepared has the composition: 50% by weight of NiO, 17% by weight of CuO, 1.5% by weight of $MoO_3$ and 31.5% by weight of $ZrO_2$. The reduction is carried out at 290° C., the heating rate being 3° C./minute. Reduction was effected first with 10% $H_2$ in $N_2$ for 50 minutes, then with 25% $H_2$ in $N_2$ for 20 minutes, then with 50% $H_2$ in $N_2$ for 10 minutes, then with 75% $H_2$ in $N_2$ for 10 minutes and finally with 100% $H_2$ for 3 hours. The percentages are each percentages by volume. The passivation of the reduced oxidic species is carried out at room temperature in dilute air (air in $N_2$ with an $O_2$ content of not more than 5% by volume).

EXAMPLE 2

Preparation of Amination Catalyst (i)

A solution composed of 132 ml of water, 27.84 g of $Ni(NO_3)_2 \cdot 6H_2O$, 61.68 g of $Cu(NO_3)_2 \cdot 2\frac{1}{2}H_2O$ and 3.52 g of $AgNO_3$ is prepared. 200 g of $ZrO_2$ support material are impregnated with half of the impregnation solution and then dried under air at 120° C. for 12 h. Thereafter, the catalyst is impregnated with the rest of the impregnation solution and dried under air at 120° C. for 12 h. The catalyst is then calcined at 400° C. for 4 h. The catalyst thus formed comprises 7.3% by weight of Cu, 2.4% by weight of Ni and 0.98% by weight of Ag.

EXAMPLE 3

Preparation of Oxidation Catalyst (ii)

Pt Impregnated on $Al_2O_3$

Platinum nitrate (the amount of platinum nitrate arises from the composition of the catalyst system obtained) was dissolved in distilled water so as to form a 2% by weight aqueous solution. An $Al_2O_3$ support material is impregnated with this solution. After drying at 120° C. and calcining at 450° C. for 4 hours, a catalyst system comprising 0.001-0.1% by weight of Pt is obtained, Pt together with the support material adding up to 100% by weight.

What is claimed is:

1. A process for aminating at least one aromatic hydrocarbon with ammonia in the presence of a catalyst (i) which catalyzes the amination, which process comprises
supplying an oxidizing agent to a reaction mixture comprising the aromatic hydrocarbon and
reacting the oxidizing agent with hydrogen which is formed in the amination in the presence of a catalyst (ii) which catalyzes the reaction of the oxidizing agent with hydrogen.

2. The process according to claim 1, wherein the aromatic hydrocarbon is first reacted with ammonia in the presence of the catalyst (i) and the oxidizing agent is then supplied to the reaction mixture.

3. The process according to claim 1, wherein the aromatic hydrocarbon is first reacted with ammonia in the presence of the catalyst (i) and then, in the presence of the catalyst (ii), the hydrogen formed is removed from the reaction mixture with the oxidizing agent, wherein the hydrocarbon reacts with ammonia in the presence of the catalyst (i) during the hydrogen oxidation.

4. The process according to claim 1, wherein the aromatic hydrocarbon is reacted with ammonia in the presence of the catalyst (i) in a first reaction chamber, then the oxidizing agent is supplied to the reaction mixture and, in a subsequent reaction chamber, the oxidizing agent is reacted with the hydrogen formed in the amination in the presence of the compound (ii) which catalyzes this reaction with hydrogen, wherein the hydrocarbon reacts with ammonia in the presence of the catalyst (i) during the hydrogen oxidation.

5. The process according to claim 1, wherein the catalysts (i) and (ii) are each present in separate catalyst beds, the oxidizing agent is supplied to the reaction mixture upstream of a catalyst bed comprising the catalyst (ii), and the catalyst bed comprising the catalyst (ii) is followed by a catalyst bed comprising the catalyst (i).

6. The process according to claim 1, wherein the catalyst (i) comprises compounds which comprise Ni, Co, Fe, Cu or combinations of these elements.

7. The process according to claim 1, wherein the catalyst (i) comprises compounds which comprise Ni—Cu—X, Fe—Cu—X and/or Co—Cu—X, in which X is Ag or Mo.

8. The process according to claim 1, wherein the catalyst (ii) comprises compounds comprising at least one of Pt and Pd, and Ag.

9. The process according to claim 1, wherein the proportion by weight of the elements Ni, Co and Fe together in catalyst (i) is between 0.1% by weight and 75% by weight, and the proportion by weight of Cu is between 0.1% by weight and 75% by weight, based in each case on the total weight of catalyst (i).

10. The process according to claim 7, wherein the proportion by weight of the doping element X in the total weight of the catalyst (i) is between 0.01% by weight and 8% by weight based on the total weight of the catalyst (i).

11. The process according to claim 8, wherein the proportion by weight of Pt in catalyst (ii) is between 0.0001% by weight and 1% by weight, based on the total weight of catalyst (ii).

12. The process according to claim 1, wherein a catalyst bed comprising catalysts (i) and (ii) is loaded with an hourly space velocity of from 0.1 to 5 kg of the aromatic hydrocarbon per liter of catalyst bed and per hour.

13. The process according to claim 1, wherein the amination is performed continuously.

14. The process according to claim 1, wherein hydrogen is removed physically from the reaction mixture.

15. The process according to claim 14, wherein the amination is effected in a membrane reactor with integrated hydrogen removal by a hydrogen-permeable membrane.

16. The process according to claim 1, wherein the amination is performed at temperatures between 200 and 800° C.

17. The process according to claim 1, wherein the amination is performed at pressures between 1 and 900 bar.

18. The process according to claim 1, wherein one molar equivalent of the aromatic hydrocarbon is reacted with one molar equivalent of ammonia to form one molar equivalent of an aminated aromatic hydrocarbon and one molar equivalent of hydrogen.

19. The process according to claim 1, wherein the aromatic hydrocarbon is benzene and the amination forms aniline.

20. The process according to claim 1, wherein the catalyst (i) comprises Mi, Cu, Zr and Mo, and the catalyst (ii) comprises Pt.

* * * * *